(12) United States Patent
Cennamo

(10) Patent No.: US 12,318,078 B2
(45) Date of Patent: Jun. 3, 2025

(54) MANUAL OPERATION UNIT, AND MANUAL OPERATION GROUP FOR A MEDICAL DEVICE

(71) Applicant: ENDOKEY S.R.L., Bologna (IT)

(72) Inventor: Vincenzo Cennamo, Bologna (IT)

(73) Assignee: ENDOKEY S.R.L., Bologna (IT)

( * ) Notice: Subject to any disclaimer, the term of this patent is extended or adjusted under 35 U.S.C. 154(b) by 1040 days.

(21) Appl. No.: 17/047,252

(22) PCT Filed: Apr. 12, 2019

(86) PCT No.: PCT/IB2019/053038
§ 371 (c)(1),
(2) Date: Oct. 13, 2020

(87) PCT Pub. No.: WO2019/198049
PCT Pub. Date: Oct. 17, 2019

(65) Prior Publication Data
US 2021/0153853 A1 May 27, 2021

(30) Foreign Application Priority Data
Apr. 13, 2018 (IT) .................. 102018000004478

(51) Int. Cl.
*A61B 17/00* (2006.01)
*A61B 1/018* (2006.01)

(52) U.S. Cl.
CPC ........ *A61B 17/00234* (2013.01); *A61B 1/018* (2013.01); *A61B 2017/00296* (2013.01); *A61B 2017/00336* (2013.01); *A61B 2017/0034* (2013.01); *A61B 2017/00358* (2013.01); *A61B 2017/00438* (2013.01); *A61B 2017/00818* (2013.01)

(58) Field of Classification Search
CPC .............. A61B 17/00234; A61B 1/018; A61B 2017/00296; A61B 2017/00336; A61B 2017/0034; A61B 2017/00358; A61B 2017/00438; A61B 2017/00818
See application file for complete search history.

(56) References Cited

U.S. PATENT DOCUMENTS 6,217,587 B1 * 4/2001 Tsuruta ................ A61B 17/221
606/1
2005/0070885 A1 3/2005 Nobis et al.
(Continued)

FOREIGN PATENT DOCUMENTS

WO 2006060433 A2 6/2006
WO 2015029041 A1 3/2015
WO 2017025969 A1 2/2017

*Primary Examiner* — Joseph M Dietrich
*Assistant Examiner* — Michael T. Holtzclaw
(74) *Attorney, Agent, or Firm* — Carmel Patent Agency; Robert Ballarini

(57) ABSTRACT

A manual operation unit and a manual operation group of a medical device (D), which can be used on an endoscope (E); wherein the operation unit (2) has a supporting body (7; 121; 121'; 121b'), which is configured to adhere, in use, to an area of the user's hand, in particular a finger; and a retaining portion (8; 122a; 122a'; 122b'), which is connected to said supporting body (7; 121; 121'; 121b') and configured to be hooked, in use, to the medical device (D).

26 Claims, 9 Drawing Sheets

(56) References Cited

U.S. PATENT DOCUMENTS

| | | | |
|---|---|---|---|
| 2006/0116692 A1* | 6/2006 | Ward | A61B 17/2909 606/113 |
| 2006/0224041 A1* | 10/2006 | Okada | A61B 10/06 600/106 |
| 2007/0100201 A1* | 5/2007 | Komiya | A61B 1/00133 600/106 |
| 2012/0046667 A1* | 2/2012 | Cherry | A61B 17/221 606/113 |
| 2016/0331468 A1* | 11/2016 | Lee | A61B 17/00234 |
| 2017/0319221 A1* | 11/2017 | Chu | A61B 17/2909 |
| 2019/0083116 A1* | 3/2019 | Mansfield | A61B 17/00234 |

* cited by examiner

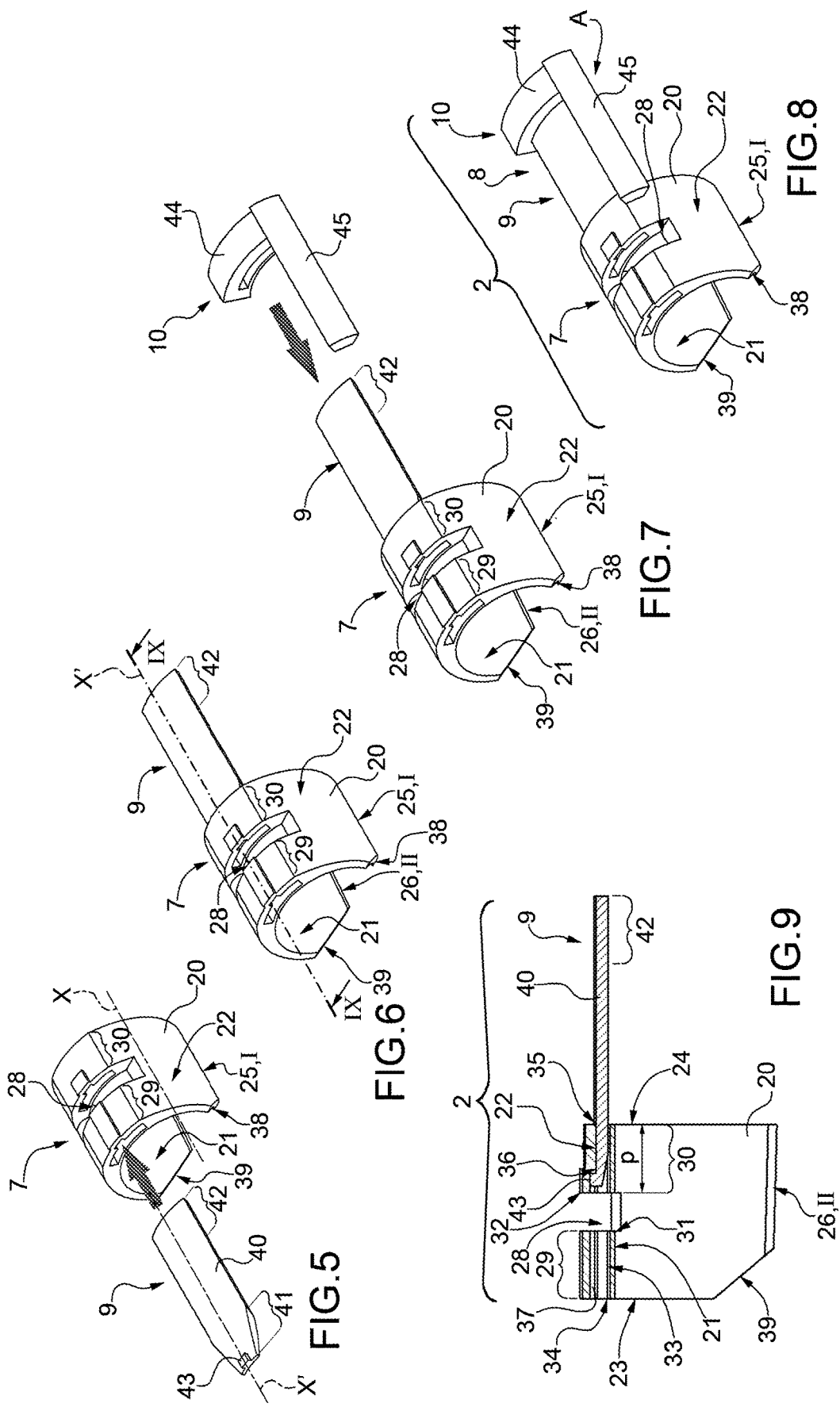

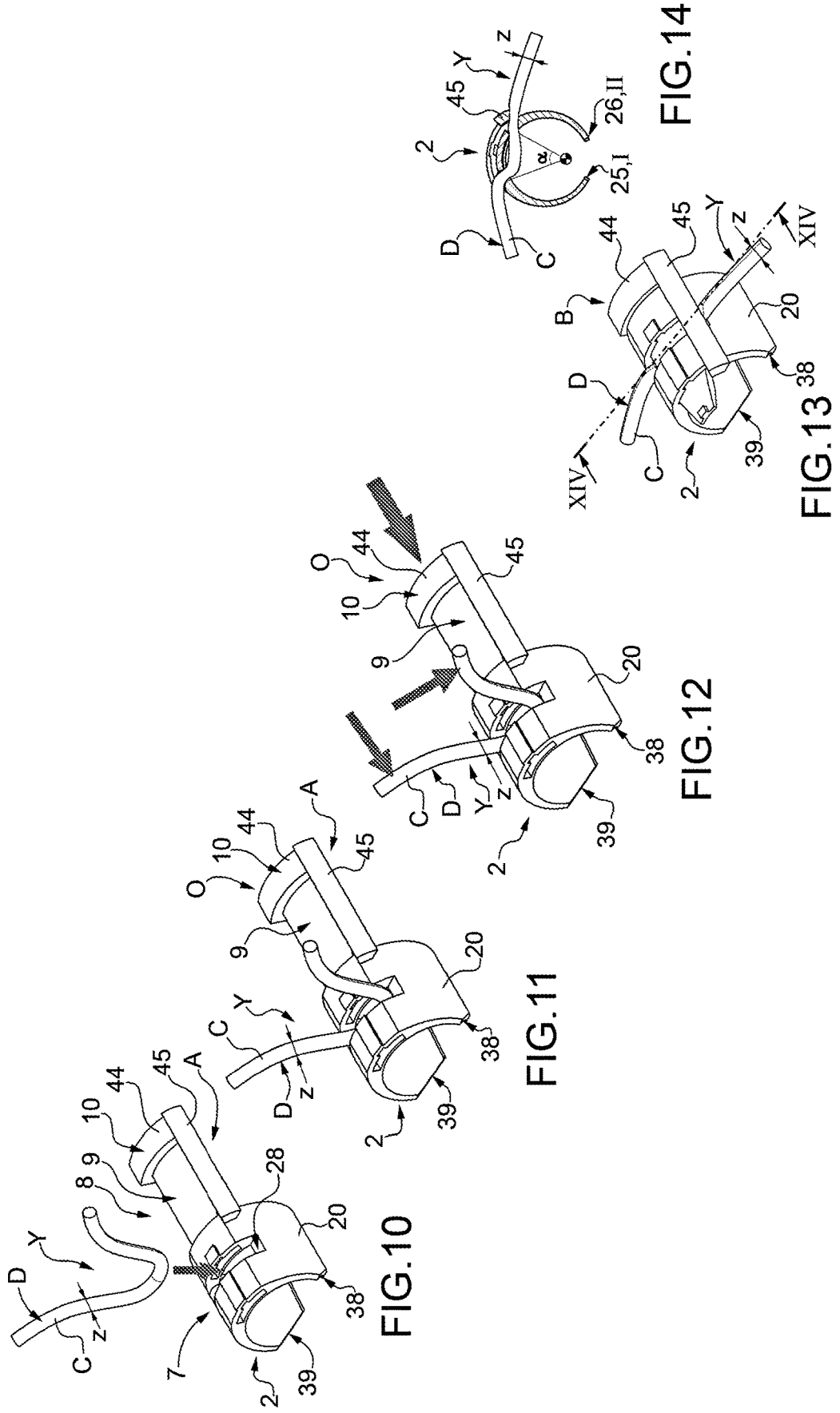

MANUAL OPERATION UNIT, AND MANUAL OPERATION GROUP FOR A MEDICAL DEVICE

CROSS-REFERENCE TO RELATED APPLICATIONS

This Patent Application claims priority from Italian Patent Application No. 102018000004478 filed on Apr. 13, 2018, the entire disclosure of which is incorporated herein by reference.

TECHNICAL FIELD

The present invention relates to a manual operation unit and a manual operation group for a medical device, which can be used with an endoscope.

In particular, the present invention relates to a manual operation unit and a manual operation group, i.e. which are configured to allow an operator to move axially and operate manually, with only one hand, a medical device, such as, for example a polypectomy snare, while carrying out an endoscopy, without the aid of motors or servo controls.

Operators who perform the endoscope examination, with one hand always engaged in gripping, holding and managing the endoscope, have only one hand free with which to insert, move and operate the medical devices, which can be used with an endoscope.

Generally, a medical device for an endoscopy comprises a sheath and an operating instrument, which is contained inside the sheath and by means of which it is fastened to a handle containing actuators. An operating instrument can be assemblable or it is already factory assembled to an actuator handle. In use, the sheath is made to slide through an endoscope by means of a special channel thereof and, in use, upon exiting the endoscope, it is pushed, in a known manner, into the body of the patient (along a lumen) reaching a predetermined position; at a second stage, the operating instrument is pushed outside using the handle.

The operating instrument is constrained, at least partially, to the sheath, so that the axial movement of the sheath along the tube of the endoscope causes a corresponding axial movement of the operating instrument along said tube. The operating instrument comprises an operating end, which exits the sheath in the body of the patient.

The actuation of the operating instrument corresponds to an operating movement of the operating end, which is independent (at a kinematic level) with respect to such axial movement of the operating instrument.

During the endoscopic procedure using the medical device, for the correct operation of the device, a constant dynamic coordination between the bi-directional axial movements—backwards and forwards—performed by pushing and pulling on the sheath, and the operating movements, performed by actuating the actuators placed in the handle, is essential. The two types of movements must be strictly coordinated, complementary as well as simultaneously implementable.

It is particularly difficult for one user to cause, with the same hand, the actuation of the operating instrument by acting on the actuator handle, which is integrated or assemblable with the medical device (usually with a structure having three rings: one for the thumb, one for the index finger and another one for the middle finger) and the aforesaid axial movement of the sheath, carried out due to the grip exerted by the user with two or three fingers (thumb and index finger or index finger and middle finger) on the sheath at a distance of a few centimetres from the proximal access of the channel for devices in the endoscope. Therefore, according to the known techniques, in order to be able to perform both operations (for example during a polyp resection) a first user is needed for the axial movement of the sheath, and a second user, i.e. an assistant, is needed to actuate the operating instrument by means of the actuator handle.

Since the actuation of the operating instrument and the axial movement of the sheath are frequently required to be complementary, it is determined that such simultaneity requires maximum coordination, which, when two users are using the device, relies exclusively on the effective communication between the first user and the second user, with potential misunderstandings or latency between the voice commands and actions performed.

The operation may be further complicated by the fact that the users involved may speak different languages; therefore, the communication between the two users may not be clear and accurate.

Furthermore, the choice of the type of movement and method of actuating the operating instrument, for which the first user is responsible, depends both on the endoscopic display and on the continuous and precise feedback sent by the accessory, by mechanical transmission, to the user's mechanoreceptive sensibility (which comprises tactile and positional sensibility), which receives as stimulus the mechanical stress to which the accessory is subjected during the use, for example linked to the different resistance encountered based on the different tissue consistency.

Both the sheath and the present handles currently used, are effective in sending precise feedback from the device to the user's sensibility, by mechanical transmission to the user's mechanoreceptive sensibility.

At the current state, it is extremely difficult to transmit subjective mechanoreceptive sensations perceived by the second user, or assistant, to the first user, who is manoeuvring the axial movements of the sheath. Consequently, the user responsible for the manoeuvre cannot perceive the important information relating to the sensibility perceived by the second user, who is assisting him/her, who can only provide vocal information relating to his/her perceptions, which has ear limitations.

However, the mechanoreceptive sensibility perceived both by gripping the sheath and by holding the handle, are decisive, in particular equally essential, in determining changes in the method and timing of performing the surgery (such as the resection of a polyp), and they are essential for the correct execution of the surgery, thus avoiding complications (for example: excessive bleeding; excessive thermal transmission in depth in the surrounding tissues with the consequent risk of perforation; resection of an excessive quantity of tissue; failed coordination between the opening/closing movement of the instrument and the backward/forward movement of the sheath and/or the instrument).

Failure to convey all sensitive feedback and actions to one single user, determines aspects of elevated clinical risk relating to reduced safety of the overall essential coordination, with latency between the requests for action made by the first user to the second one and the reaction time to the request; problems of understanding the sensations and actions requested, in quantitative and qualitative terms, or even the risk of incorrect communication or misunderstandings; reduced precision of such movement according to the different needs, which can change in real time. Furthermore, the shared use of accessories which determine risky therapeutic actions, such as the removal of polyps, the positioning of clips, resections, cauterisations etc. determine complex scenarios of attributing responsibilities, both in a general sense and in the case of complications and relative cases. In fact, in an endoscopy, the first user, as the executor, is responsible for the clinical act, whereas, with the current operating methods, it is actually determined by a joint action, where the second user, in most cases represented by another person, usually a nurse, who determines important clinical actions, may not be specifically authorised to perform medical procedures, in accordance with the different legislation.

In this regard, in the latest statistical data, it is evidenced how technologies of the known type, for example in the case of polyp resections, lead to complications, such as bleeding (between 0.2 and 24% of the cases) and perforations (1%). Furthermore, 5% of perforations are lethal.

This has led to an elevated number of compensation claims and an increasing number of malpractice cases, wherein "procedural errors" are indicated as possible causes of the damage in 25% of the cases. At the same time, while the responsibility lies with the first user, so that it is compulsory for said user to comply with the good clinical practices recommended by the guidelines, and report his/her procedural work for an appropriate management of the clinical risk and possible related legal aspects, the crucial procedural aspects carried out by the assistant are well known in literature. Furthermore, the assistant's experience has been related to the risk of complications.

PRIOR ART

The use is known, for example from WO2017025969 A1 or WO2015/029041 A1, of motorised appliances, i.e. comprising motorised actuators, which actuate the different components of the medical device. This type of motorised appliances comprise, for example a handle, which can be gripped by a user, and a series of commands (in the form of joysticks, levers, buttons and similar), which can be operated by the user and which are configured to generate electric signals and operate the motorised actuators. This type of motorised appliances are particularly complex, bulky and expensive. Furthermore, the known solutions of the type described above have the disadvantage of providing the user with a reduced sensibility, i.e. a poor perception of the sensations provided by the medical device inside the body (such as tissue resistance or similar) during operation, due to the interposition of several mechanical components and servo motors between the user and the medical device.

Manually operated appliances of the medical device are also known, as disclosed for example in US2005/070885 A1 or WO2006060433. A known type of manually operated appliance comprises a handle, which is configured to be gripped by a user, and commands configured to act on the medical device.

In the solutions of the known type, the commands are integrated in the handle so as to form a single united body.

To overcome the problem of joint operation with only one hand of the axial manoeuvrability of the sheath and the relative operating instrument constrained thereto and operation of the functioning of the operating instrument, both US2005/070885 A1 and WO2006060433 claim technical solutions based on new actuators to activate the functioning of the operating instrument, integrated in handles with a specific design, without the introduction of any technical solution with regard to the axial movement, which is left, both in US2005/070885 and in WO2006060433, as in the current state, to the user's digital grip.

Consequently, according to the solutions described in US2005/070885 A1 or WO2006060433, in order to move the sheath, the user is obliged to use at least two fingers, with the thumb variably associated with the index finger or the middle finger, thus excluding the possibility of using all those medical devices already in use and pre-integrated with a standard handle (generally with three rings) or assemblable with the same, which are operated by means of the same fingers (usually with a structure with three rings: the thumb, the index finger and the middle finger).

On the contrary, as will be further illustrated below, the technical solution according to the present invention overcomes this problem focusing on the simplification of the axial movement by means of a special dedicated operation unit, allowing the operation, with one hand, of medical devices already in use and pre-integrated with a standard handle.

Furthermore, known manually operated appliances are complex, equipped with several gears and bulkier than the current handles. Therefore, although, on the one hand, they allow the medical device to be operated with only one hand, on the other, they do not provide the user with the required mobility and sensibility due to the features of the appliance, where various components and gears are interposed at the handle.

Furthermore, the fact that the commands are integrated in the handle, creates a physical distance from the position of contact between user and appliance and the position of contact between appliance and medical device. This results in a reduced sensibility by the user.

Furthermore, for the commands which determine the cutting, i.e. the sliding of the sheath with respect to the operating instrument, the area of interaction between appliance and medical device is, in the equipment described above, far from the point in which the medical device is inserted into the endoscope. This implies both a reduced sensibility by the user and a risk of the medical device bending in the section comprised between the endoscope and the manually operated equipment.

DESCRIPTION OF THE INVENTION

It is an object of the present invention to provide an operation unit, which allows a user to perform all of the necessary operations independently, so as to overcome the problems of coordination with another user and the reporting problems, which are typical of the systems known and described above.

Contrary to what is described in US2005/070885 A1 or in WO2006060433, it is an object of the present invention to provide a manual operation unit, which can be fitted to a user's finger, which, associated by means of the same hand with any handle in use, pre-integrated or assemblable to a medical device, allows an operation group to be formed, which is able to manage, for the single user, all of the necessary movements and operations independently, thereby guaranteeing complete management of the medical device by a single user.

Advantageously, as will be further illustrated below, the operation unit, fitted onto one single finger, manages the axial movement of the sheath and the relative operating instrument of the medical device, but without limiting the bending and stretching movements of the same finger onto which it is fitted, or involving other fingers in the axial movement of the sheath in the endoscope channel. Consequently, in use, it is easy for the user to grip and operate any medical device with any traditional type of handle, to which the operation unit could be connected, thus constituting a universal operation group formed by the operation unit, a single hand of a single user and any handle in use, i.e. any medical device with a pre-mounted handle.

Advantageously, the possibility of using devices and handles already in use, allows the application of consolidated technical principles to popular systems with extensive evidence of reliability, the efficacy and safety of which are increased by conveying the functionality to one single user. On the contrary, it is not known what the reliability, efficacy and safety of new actuators might be.

It is an object of the present invention to provide an operation unit, which allows the user to be provided with precise perceptions of the operations carried out, which are generated directly by the action of the medical device on the user's mechanoreceptive sensibility.

It is an object of the present invention to provide an operation unit, which allows a user to operate the medical device manually, guaranteeing: maximum sensibility, maximum freedom of movement and maximum comfort.

It is an object of the present invention to provide an operation group comprising any handle and an operation unit (different from the handle or connectable to the handle), which allows the complete operation of a medical device to be obtained using the fingers of one hand, preferably a single finger of the user's hand.

It is an object of the present invention to provide an operation unit and group, which overcome the problems described above.

According to the present invention an operation unit is provided according to the information stated in the appended claims.

According to the present invention an operation group is provided according to the information stated in the appended claims.

BRIEF DESCRIPTION OF THE DRAWINGS

The invention will now be described with reference to the appended drawings, illustrating non-limiting embodiments thereof, wherein.

Figure 1:
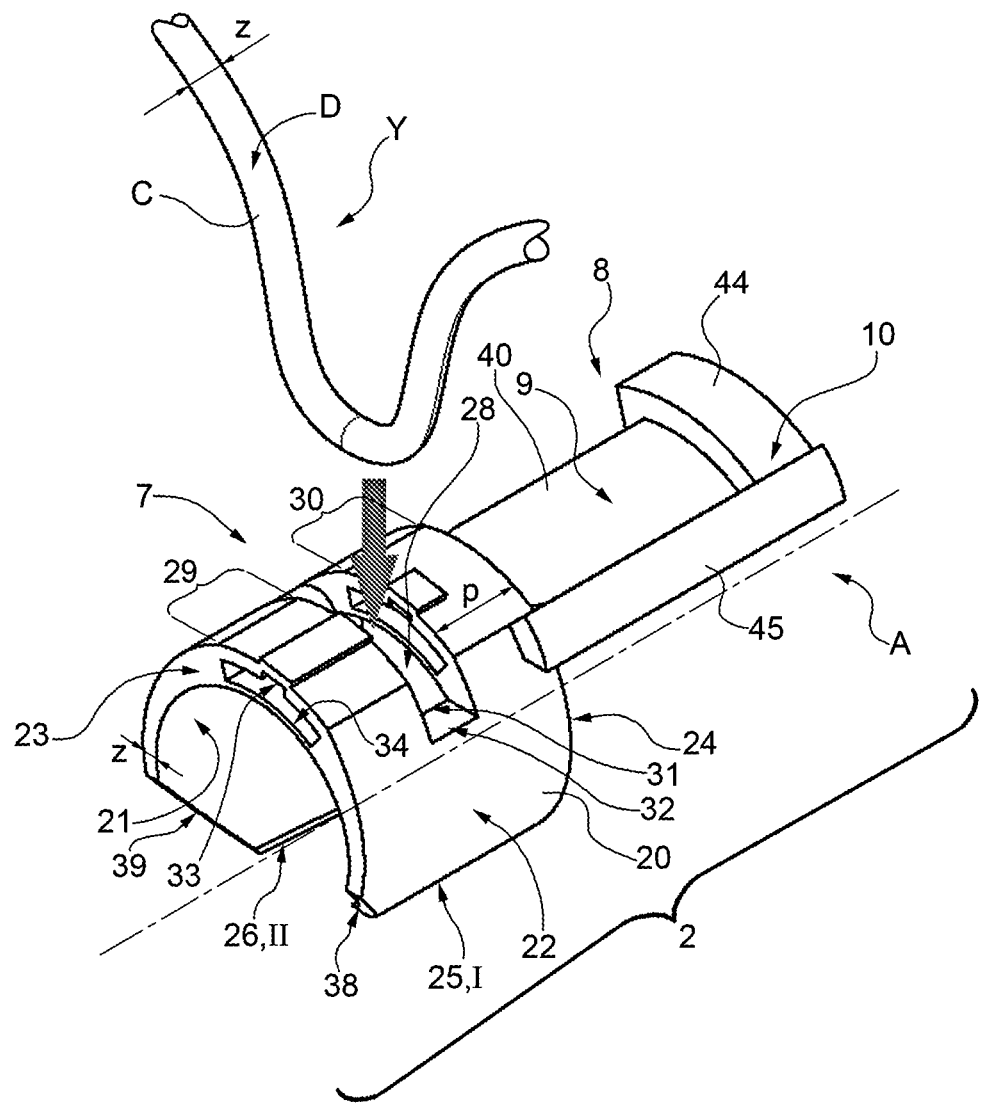
FIG. 1 is a perspective view on an enlarged scale of an operation unit according to the present invention during the hooking to a medical device.
Figure 15:
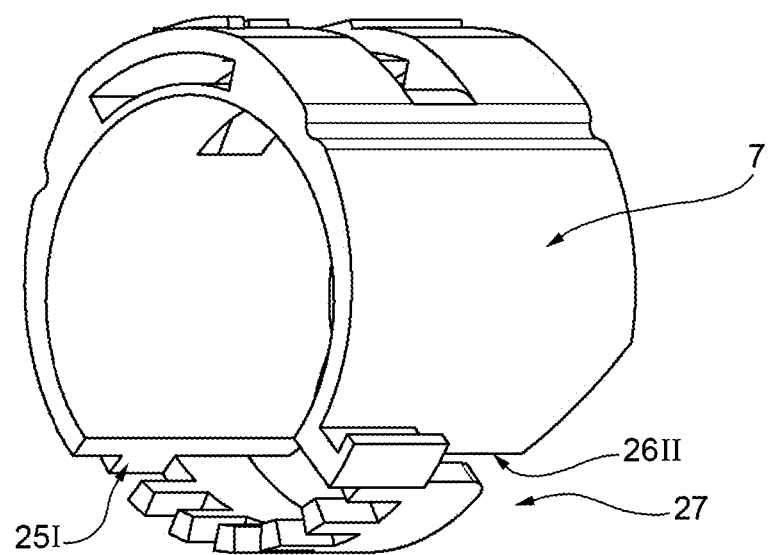
Figure 16:
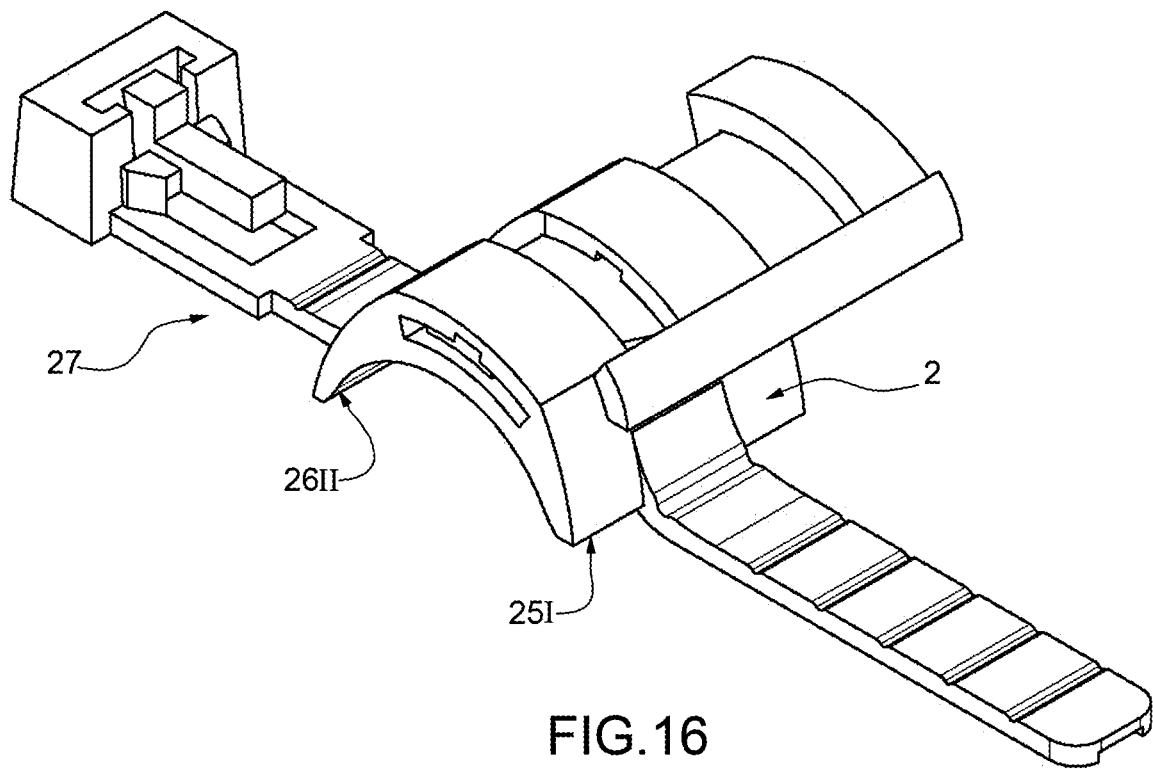
Figure 17:
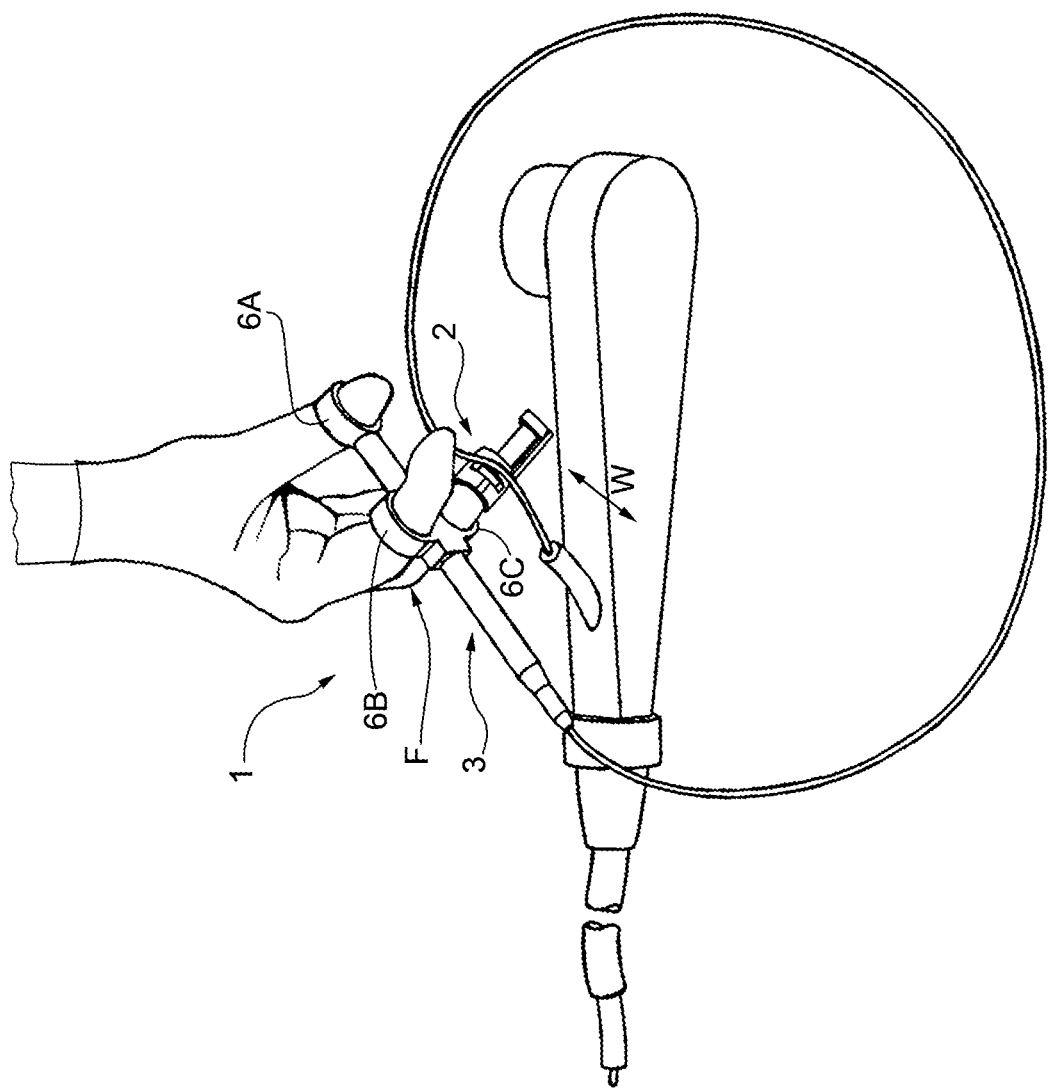
Figure 18:
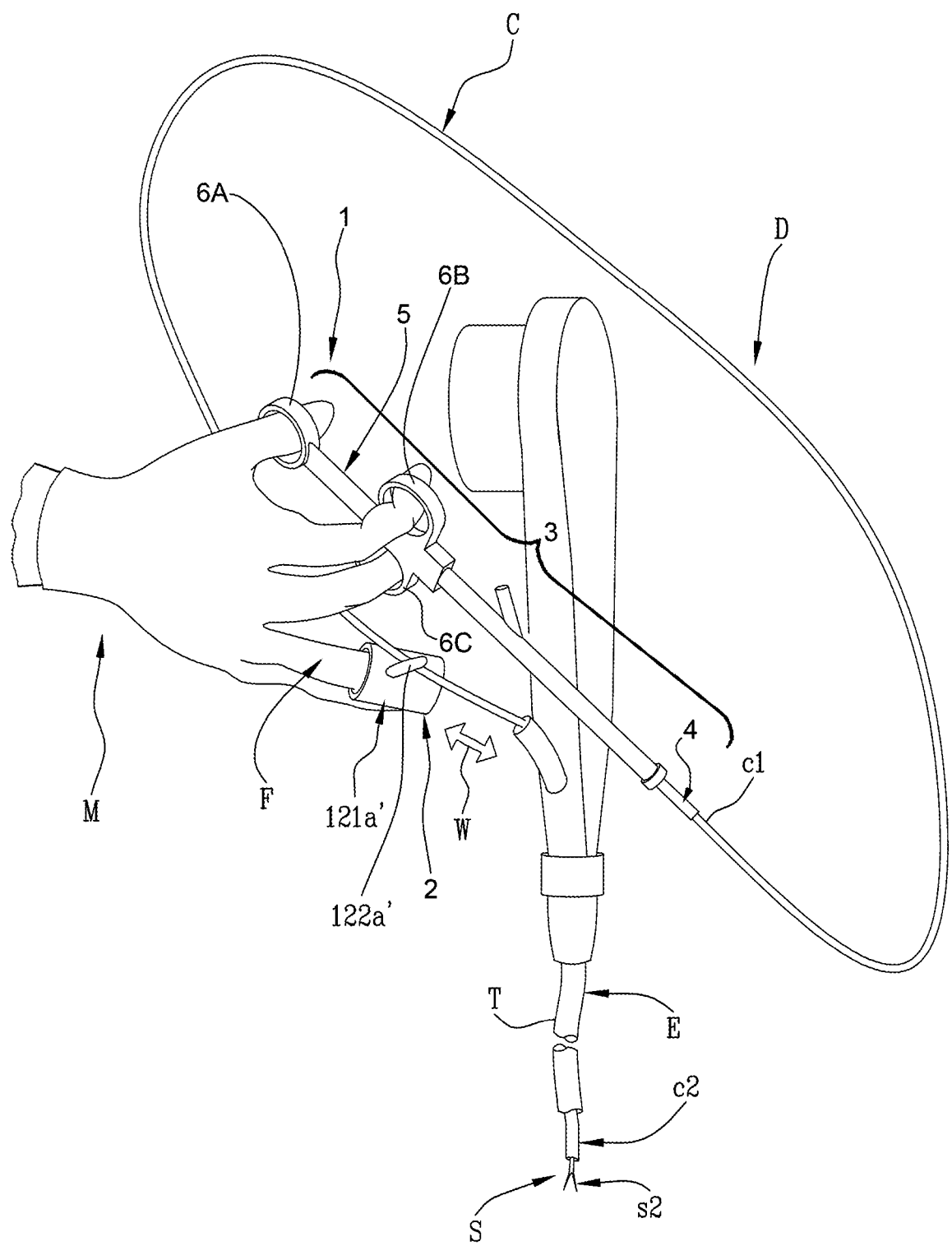
Figure 19:
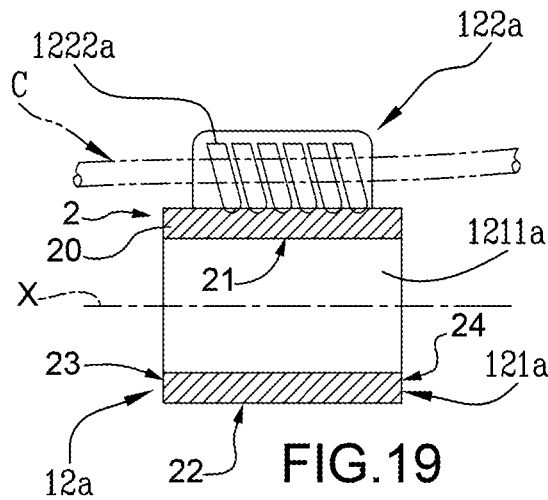
Figure 20:
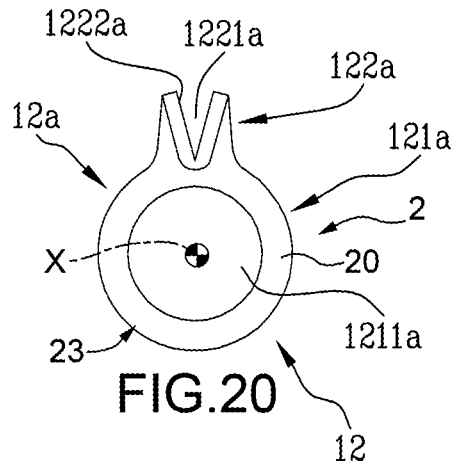
Figure 21:
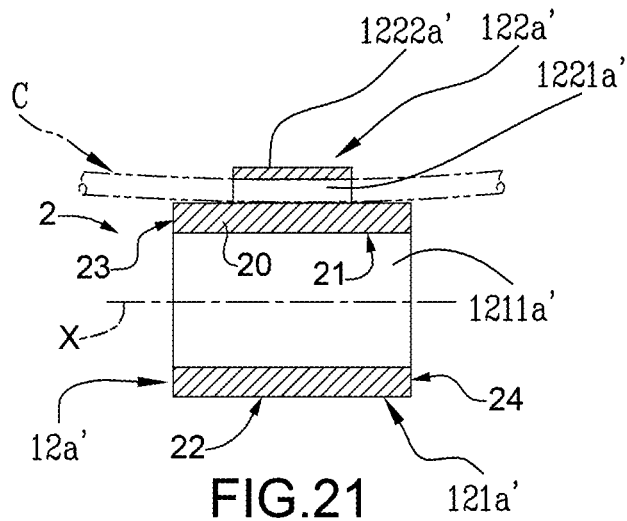
Figure 22:
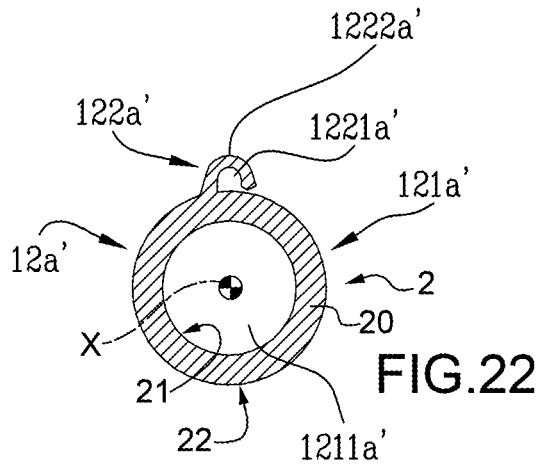
Figure 23:
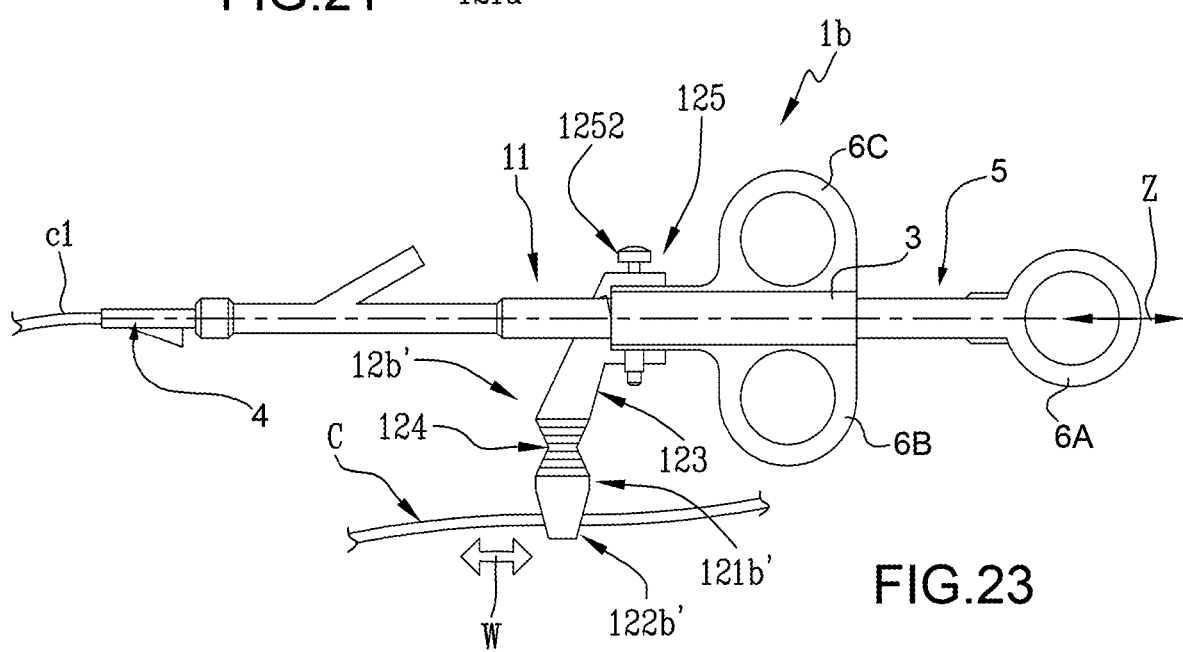
Figure 24:
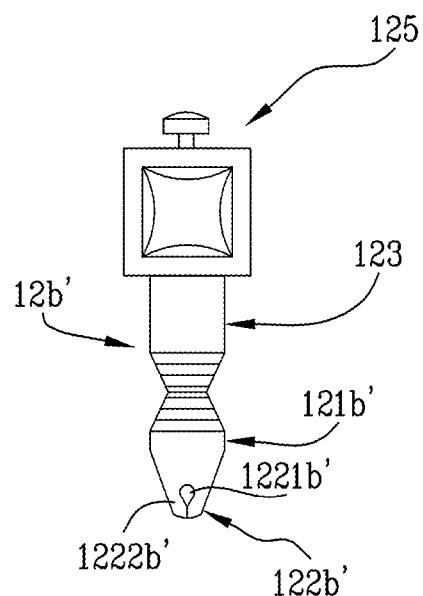
Figure 25:
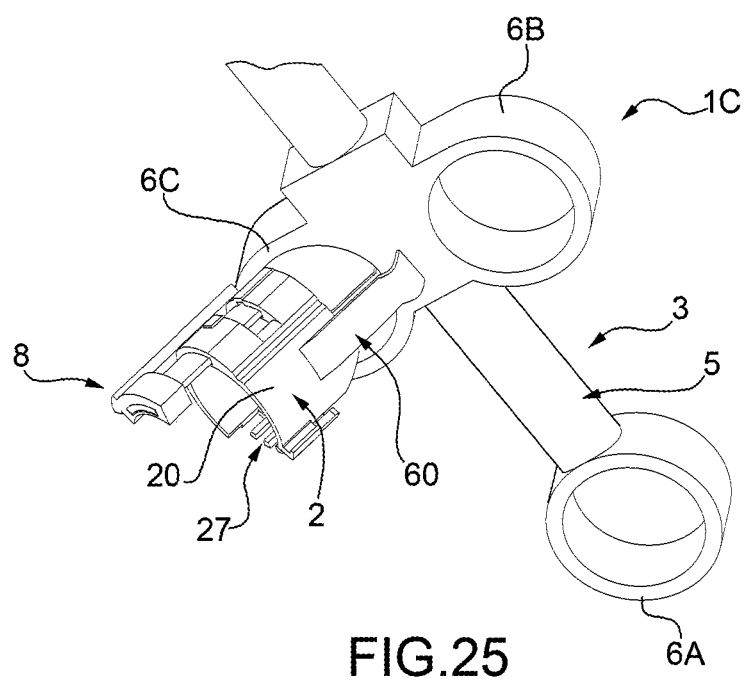

figures from 5 to 8 are views of respective different assembly steps of the details shown in figures from 2 to 4 for the assembly of an operation unit according to the present invention;

FIG. 9 is a section according to the line IX-IX and on an enlarged scale in FIG. 6;

figures from 10 to 13 show the operation unit according to the present invention in respective different operating configurations during the step of hooking to a medical device;

FIG. 14 is a section according to the line XIV-XIV in FIG. 13;

FIG. 15 is a perspective view of a variation of the operation unit shown in figures from 1 to 14;

FIG. 16 is a perspective view of a further variation of the operation unit shown in figures from 1 to 14; and FIG. 17 shows an operation group comprising an operation unit according to the illustration in FIG. 1;

FIG. 18 is a schematic view of a variation of the operation unit according to the present invention, whereas, in use, it forms, with a handle, a first embodiment of an operation group according to the present invention;

FIG. 19 is a partially sectional side view of the operation unit in FIG. 18;

FIG. 20 is a front view of the operation unit in FIG. 19;

FIG. 21 is a longitudinal section of a second variation of an operation unit according to the present invention;

FIG. 22 is a cross section of the operation unit shown in FIG. 21;

FIG. 23 is a schematic view of a second embodiment of an operation group according to the present invention; and, FIG. 24 is a side view, on an enlarged scale, of a detail in FIG. 23;

FIG. 25 is a schematic view of a further embodiment of an operation group according to the present invention.

In FIGS. 17 and 18, number 1 indicates, as a whole, an example of a manual operation group 1 according to the present invention.

BEST MODE FOR CARRYING OUT THE INVENTION

As shown in FIGS. 17 and 18, an operation group 1 comprises a manual operation unit 2 and a handle 3, which can be operated manually. It is specified that the expressions "manual" and "operated manually" are understood to mean that both the operation unit 2 and the handle 3 can be operated directly by an operator without the aid of motors or servo controls.

According to the example shown in FIGS. 17 and 18, advantageously, the operation unit 2 is a different body, i.e. separate from the handle 3.

According to the variation shown in FIG. 23, the operation unit 2 (or 12b' in FIGS. 23 and 24) can be connected to the handle 3, as will be better illustrated below.

Advantageously, the manual operation group 1 is configured to allow a user to operate a medical device D, which is generally used with an endoscope E (of the known type and illustrated schematically) using only one hand. In general, as illustrated in greater detail in FIG. 18, a medical device D comprises a sheath C and an operating instrument S. The sheath C is elongated. The sheath C can be, for example a catheter. The operating instrument S is inserted through the sheath C.

As shown in FIG. 18, the handle 3 comprises an attachment 4, which is configured to be coupled with a proximal end of the medical device D, and an actuator 5. In other words, the attachment 4 is configured to transfer the movement of the actuator 5 to the proximal end of the medical device D. According to the illustrated examples, the actuator 5 is of the syringe type. In particular, the actuator 5 comprises one or more interfacing elements, each of which is configured to interact with the user's hand (according to the illustrated example the right hand). The interfacing elements can be, for example rings, buttons, projections or similar.

The illustrated example shows an actuator 5 comprising three rings 6A, 6B, 6C, configured to receive the thumb, the index finger and, the middle finger of the user's right hand respectively.

The handle 3, in particular the actuator 5, is configured to allow a user to activate an operating instrument S by acting on the interfacing elements.

According to the illustration in FIG. 18, the operating instrument S comprises a respective proximal end and a respective distal end s2. The operating instrument S is elongated from the proximal end thereof (of the known type and not illustrated) to the distal end thereof s2. The distal end s2 of the operating instrument S is an operating end, so that the actuation of the operating instrument S corresponds to an operating movement of such operating end s2.

The sheath C comprises a respective proximal end c1 and a respective distal end c2. The sheath C is elongated from the proximal end thereof to the distal end thereof.

The operating instrument S is inserted along the inside of the sheath C, so as to cross the sheath C from the proximal end c1 of the sheath C to the distal end c2 of the sheath C.

A distal end sector of the device D comprises the distal end s2 of the operating instrument S and the aforesaid distal end c2 of the sheath C.

The distal end s2 of the operating instrument S protrudes, in turn, from the distal end c2 of the sheath C.

The device D is therefore elongated from the proximal end s1 of the operating instrument to the distal end s2 of the operating instrument.

The device D operatively crosses the tube T of the endoscope E longitudinally so that the end sector of the device D protrudes with respect to the tube T of the endoscope E, so as to be able to be situated inside the body of a patient.

In FIG. 18 the tube T is shown as split to adapt the size thereof to the space in the figure.

When the handle 3 is coupled to the medical device D, both the sheath C and the operating instrument S are connected to the handle 3, in particular to the actuator 5. In this condition, the proximal end c1 of the sheath C and/or the proximal end of the operating instrument S are connected to the handle 3.

The axial movement of the sheath C is considered below as the movement of the sheath C along the elongation thereof. Similarly, the axial movement of the operating instrument S is considered as the movement of the operating instrument S along the elongation thereof.

The operating instrument S is at least partially constrained to the sheath C, so that the axial movement of the operating instrument S corresponds to the axial movement of the sheath C.

The actuation of the operating instrument S could involve relative movements between the operating instrument S and the sheath C. Consequently, the operating instrument S is constrained to the sheath C so that the relative movements are nonetheless allowed, regardless of the fact that the axial movement of the sheath C causes a corresponding axial movement of the operating instrument S.

The user may also need to cause, besides actuation of the operating instrument S and, possibly, simultaneously with such actuation, the axial movement of the sheath C, in order to regulate the positioning of the operating end s2 in the patient's body.

The operation group 1 according to the present invention is configured so that a user can operate, with the same hand M and, if necessary, simultaneously with the actuation of the operating instrument S, also the axial movement of the sheath C.

In FIG. 1, a manual operation unit 2 according to the present invention is indicated with 2. The operation unit 2 is configured to be applied to a Y portion of a medical device D and to be operated directly by a user. By directly we mean manually, without the use of intermediate actuators. As will be better illustrated below, the operation unit 2 is configured to be applied, advantageously, to a phalanx of a finger, which is also used to operate an actuator 5 of any type of handle 3. In other words, as shown in FIG. 17, the operation unit 2 is configured to be applied to a phalanx of a finger (in the illustrated example the middle finger), which interfaces simultaneously with an actuator 5 (in the illustrated example the ring 6C) of a handle 3.

Therefore, advantageously, by means of the operation unit 2, with one single finger, a user can obtain the simultaneous actuation of the operating instrument S and the axial movement of the sheath C.

The operation unit 2 comprises a supporting body 7 and a retaining portion 8. The supporting body 7 is configured to be applied to a hand, generally a user's gloved hand. Advantageously, the supporting body 7 is configured to engage only one phalanx of a user's finger.

The retaining portion 8 is configured to be applied to a Y portion of a medical device D, as will be better illustrated below.

The operation unit 2 according to the present invention is configured to adhere to the user's gloved hand (during an operation the user's hands are covered with thin latex gloves), so as to allow maximum sensibility during operation of the medical device D.

Figure 2:
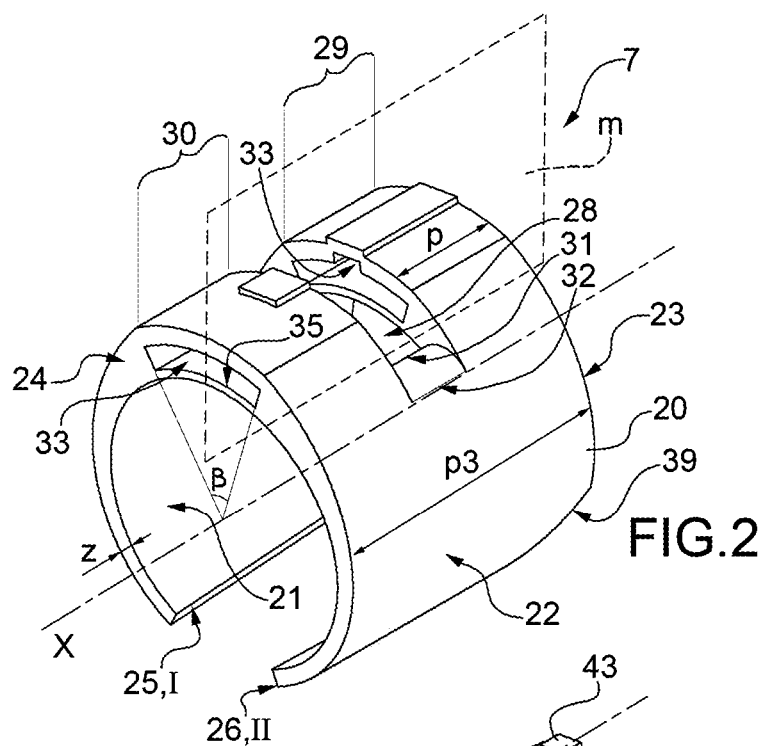
FIG. 2 is a perspective view of a first detail in FIG. 1.

Preferably, according to the illustration in FIG. 2, the supporting body 7 is configured to be fitted about the user's finger, preferably about a single phalanx, preferably the ungual phalanx.

Advantageously, the operation unit 2 being fitted only on the ungual phalanx (or terminal phalanx) on only one finger of the hand, allows the articulation of the movements of the finger since the flexion-extension of the articulations of the three phalanxes: proximal (or phalanx properly called), middle (or second phalanx) and distal (ungual phalanx).

In this way, when a user fits the operation unit 2 he/she can articulate the finger freely, consequently, he/she is able to perform all possible finger movements, including bending and stretching. Consequently, the operation unit 2 gives the user the possibility to perform a further movement, such as operating an actuator 5 of a handle 3. The retaining portion 8 and the supporting body 7 are mutually movable with respect to each other.

According to the example illustrated in figures from 1 to 17, the retaining portion 8 comprises a pin 9 and a support 10, which are movable with respect to the supporting body 7, as will be better illustrated below.

According to the embodiment illustrated in figures from 1 to 17, the supporting body 7 comprises a curved wall 20 having a longitudinal axis X. The curved wall 20 has an inner surface 21, an outer surface 22, a proximal surface 23, a distal surface 24, a right side surface 25 and a left side surface 26. The terms "inner" and "outer", "right", "left", "proximal", "distal" are used with reference to the orientation of the operation unit 2 when it is fitted correctly, in use, on a finger of a user's right (gloved) hand. In other words, the inner surface 21 is the surface, which is directly in contact with the user's finger (during operation, the gloved finger), while the outer surface 22 faces outwards. The proximal surface 23 is the one closest to the palm of the hand, while the distal surface 24 is the one closest to the tip of the fingers.

According to the illustrated example, the curved wall 20 is open, i.e. it has a longitudinal interruption, and it has two ends, which are identified below with I and II. The fact that the curved wall 20 is open allows small adjustments to the supporting body 7 on the user's finger, in use.

According to the variations illustrated in FIGS. 15 and 16, the supporting body 7 comprises an adjustment unit 27, which connects the ends I and II. The adjustment unit 27 is configured to connect and optionally vary the distance between the ends I and II. Advantageously, the adjustment unit 27 allows the inner surface 21 of the curved wall 20 to be made to adhere to the user's gloved finger, so as to guarantee maximum sensibility by the user during operation of the medical device D by means of the operation unit 2. In particular, the operation unit 2 allows said sheath C to translate axially in one direction or in an opposite direction, depending on whether the finger bends or stretches, as schematised by the double arrow W in FIGS. 17, 18 and 23.

One type of adjustment unit 27 is shown in FIG. 15, comprising a curved and indented band fixed to one end and a projection fixed to the opposite end. The indented band is configured to interact with the projection and the internal diameter of the operation unit 2 depends on the indent, which engages said projection.

A further type of connection unit 27 is shown in FIG. 16, comprising two bands, which are preferably elastic, each of which is connected to a respective end of the operation unit. The internal diameter of the operation unit 2 in this case depends on the interaction between the two bands indicated above.

Only some examples of connection units 27 are shown in FIGS. 15 and 16, which can be chosen from a group of connection units, which differ from one another in: shape, size and method of coupling/interlocking with the ends of the operation unit 2.

According to a non-illustrated variation, the curved wall 20 has a disc section, in other words, the curved wall 20 is a cylindrical body closed with a internal cylindrical cavity 33.

According to the illustrated example, the thickness z of the curved wall 20 is variable, in particular it increases from each end I, II until a midplane m of the curved wall 20 (FIG. 2).

Furthermore, the curved wall 20 has a housing 28, which is configured to house, in use, at least partially, the Y portion of the medical device D. The housing 28 is substantially transverse to the longitudinal axis X.

The housing 28 is substantially in an intermediate position, along the longitudinal axis X, of the curved wall 20. In particular, the housing 28 locally divides the curved wall 20 in a proximal part 29 and a distal part 30.

Advantageously, the depth p of the distal part 30 is from 2 to 4 cm, preferably, it is from 2.5 to 3 cm. The depth p, or extension along the longitudinal axis X, of the distal part 30 is an element of reference for determining the positioning of the operation unit 2 with respect to the entrance point of the medical device D inside the endoscope E. In this way, in use, a user can verify whether he/she has positioned the operation unit 2 correctly with respect to the endoscope E or whether the operation unit 2 is too far away. In fact, if the operation unit 2 is positioned too far from the endoscope E, there is a risk of the medical device D bending beneath peak load, in the space between the operation unit 2 and the entrance of the endoscope E. Such phenomenon is undesirable and must be avoided. Therefore, the depth p of the distal part 30 allows this to be prevented from happening, acting as an element of reference for the user.

Preferably, the housing 28 is a through housing, i.e. it cuts the curved wall 20 radially for the whole of the thickness z thereof. In particular, the housing 28 faces the inner surface 21 and, the outer surface 22 respectively, through an inner opening 31 and an outer opening 32.

Advantageously, the fact that the housing 28 faces the inner surface 21 through the inner opening 31 enables the Y portion of the medical device D to come into contact, in use, with the user's gloved finger. In this way, a practically direct contact is ensured (the latex glove is extremely thin and deformable) between the Y portion of the medical device D and the user's skin, thus guaranteeing maximum sensibility for the user during operation of the medical device D.

According to the example illustrated in figures from 1 to 17, the housing 28 substantially corresponds to a removed segment of the curved wall 20, i.e. to an arch, which corresponds to an angle in the centre α from 30° to 45° on the longitudinal axis X (FIG. 14).

The housing 28 has a depth p, i.e. an extension along the longitudinal axis X, which is greater or equal to the maximum thickness z of a medical device D.

In this way, the operation unit 2 can be used with any type of medical device D already in use.

Furthermore, the curved wall 20 has a cavity 33, which is configured to house the pin 9 and to allow the pin 9 a displacement, in use, from an open position A (illustrated in FIGS. 1, 8 and 11) to a closed position B (illustrated in FIG. 13), and vice versa.

According to the example illustrated in detail in FIG. 9, the cavity 33 extends along the longitudinal axis X and is a through cavity. In particular, the cavity 33 faces outside the curved wall 20 through a proximal opening 34 (illustrated in FIG. 1) and a distal opening 35 (illustrated in FIG. 2), which are made at the proximal surface 23 and the distal surface 24 respectively. The cavity 33 has an arch section with an angle in the centre β from 20° to 30° (FIG. 2).

According to the illustrated example, the cavity 33 crosses the housing 28 in a substantially central area of the curved wall 20.

Advantageously, the curved wall 20 has a shoulder 36, which is configured to interact with the pin 9, as will be better illustrated below. According to the illustrated example, the shoulder 36 is obtained by means of a longitudinal groove 37 parallel and communicating with the cavity 33 (FIG. 9). The groove 37 faces outwardly through the proximal surface 23. Starting from the proximal surface 23, the groove 37 has a longitudinal extension, which is smaller than the extension of the cavity 33. Consequently, the shoulder 36 is a substantially radial portion of curved wall 20, at the end of said groove 37. In other words, the shoulder 36 is the bottom wall of the groove 37.

Advantageously, the curved wall 20 has a right chamfer 38, which joins the proximal surface 23 to the right side surface 25, and a left chamfer 39, which joins the proximal surface 23 to the left side surface 26. The chamfers 38, 39 are inclined by about 135° and radiant with respect to the proximal surface 23. The presence of the chamfers 38, 39 avoids interference, in use, between the curved wall 20 and the user's finger on which the supporting body 7 is fitted. In particular, the presence of the chamfers 38, 39 prevents the curved wall 20 from pushing against the user's finger, opposing resistance, on bending the finger.

Figure 3:
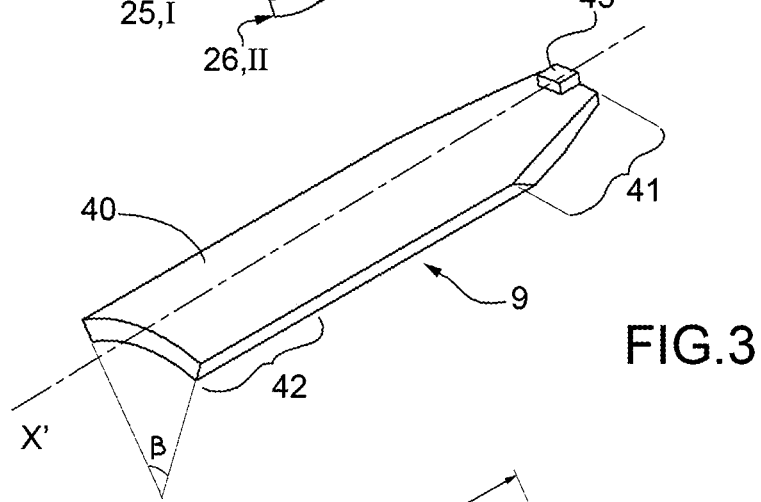
FIG. 3 is a perspective view of a second detail in FIG. 1.

According to the detailed illustration in FIG. 3, the pin 9 comprises a plate 40 having an elongated shape with a longitudinal axis X' delimited at the ends by a proximal portion 41 and a distal portion 42. The plate 40 is curved i.e. it is folded so as to have an arch section. The transverse section of the plate 40 forms an arch, which corresponds to an angle in the centre β, from 20° to 30° (FIG. 3).

The shape of the arched section of the plate 40 is similar in shape and size, to the section of the cavity 33. The shape and size of the section of the plate 40 are configured to allow the insertion of the plate 40 inside the cavity 33, so as to form a prismatic kinematic pair. In other words, the plate 40 is configured to be inserted in the cavity 33 and to allow the relative translation of the plate 40 with respect to the curved wall 20, along the longitudinal axis X'. The plate 40 further comprises a stop element 43, which protrudes from the proximal portion 41 and is configured to slide, in use, in the groove 37 and abut against the shoulder 36 of the supporting body 7.

According to the illustrated example, the cavity 33 is interposed between the groove 37 and the inner wall of the supporting body 7. The stop element 43 protrudes from the plate 40 so as to protrude outwardly, in use.

The support 10 is configured to be applied to the pin 9, so as to form a single body therewith, which is preferably indivisible.

Figure 4:
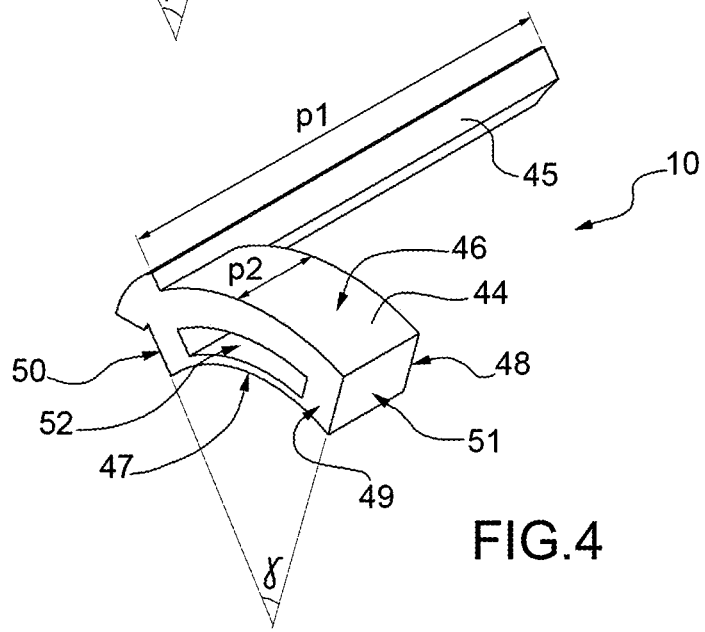
FIG. 4 is a perspective view of a third detail in FIG. 1.

The support 10 comprises a head 44 and an arm 45. The head 44 has an arched body with an angle in the centre γ, which is substantially equal to the angle in the centre β of the plate 40 (FIG. 4). The head 44 has an outer face 46, an inner face 47, a proximal face 48, a distal face 24, a right face 50 and a left face 51.

More specifically, the head 44 has a recess 52, facing outside the proximal face 23, which, in use, faces the supporting body 7. The section of the recess 52 substantially corresponds to the section of the plate 40. The shape and sizes of the recess 52 are configured to form a shape coupling and by interference with the distal portion 42 of the plate 40. In other words, after inserting the distal portion 42 of the plate 40 in the recess 52, an indivisible coupling is formed.

The arm 45 is fixed to the head 44 and protrudes from the head 44. The depth p, i.e. the extension along the longitudinal axis X, of the arm 45 is configured to allow, in use, an at least partial closing of the housing 28, as will be better illustrated below.

According to the example illustrated in figures from 1 to 13 the depth p1 of the arm 45 substantially corresponds to the sum of the depth p2 of the head 44 and the depth p3 of the curved wall 20 (FIGS. 2 and 4).

To form the operation unit 2, the distal portion 42 of the pin 9 is inserted into the proximal opening 34 on the curved wall 20. Thus, the pin 9 is made to slide in the cavity 33 until the stop element 43 is brought into contact with the shoulder 36 (FIG. 9). In this position, the proximal portion 41 of the pin 9 is contained in the proximal part 29 of the curved wall 20, while the distal portion 42 protrudes outside the distal surface 24 of the curved wall 20.

In this position, the head 44 of the support 10 is fixed to the distal portion 42 of the pin 9. The fixing is a fixing by interference, so as to prevent the support 10 from being able to slip off the pin 9 in normal use of the operation unit 2.

When the head 44 is fixed to the pin 9, the arm 45 extends along the longitudinal axis X parallel to the outer surface 22 of the curved wall 20.

The support 10 substantially acts as a support surface for the user, who can selectively regulate the opening or closing of the operation unit 2 by pushing on the head 44 on one side or on the other.

When the pin 9 is in the open position A (FIG. 12), the housing 28 of the curved wall 20 is completely free and a user is able to insert a Y portion of the medical device D in the housing 28. Advantageously, the Y portion of the medical device D must be folded in a U to be able to be inserted correctly into the housing 28 and, in particular, it must have a section, which faces or protrudes, at least partially, from the inner opening 31, so as to be placed in contact with the user's (gloved) finger.

By pushing on the head 44 of the support 10 it is possible to cause the translation of the pin 9 along the longitudinal axis X so that both the plate 40 of the pin 9 and the arm 45 of the support 10 cross the housing 28 transversely, locking the medical device D in the housing 28. FIG. 14 shows the operation unit 2 in the closed position B, wherein the medical device D is retained inside the housing 28.

Advantageously, the plate 40 of the pin 9 keeps the medical device D folded in a U-shape, guaranteeing the continuous contact, in use, of the medical device D with the user's (gloved) finger through the inner opening 31.

Advantageously, as shown in FIG. 14, the sequence of consecutive curvatures, obtained by the interaction of the medical device D with the plate 40 and the support 10, allows the translation of the medical device D to be prevented with respect to the operation unit 2.

Advantageously, the operation unit 2 of the type described above, is configured to be used as an auxiliary component, i.e. an additional accessory, of any handle 3 for an endoscope E of the traditional type and optionally already in use (FIG. 17).

In this way, it is possible to improve the efficiency of use of a traditional handle 3 already in use, by a user. The fact of comprising an independent operation unit 2 enables the implementation of handles already on the market, limiting costs as far as possible.

In use, after connecting the medical device D, in a known manner, to the actuator 5 of the handle 3, a user grips the handle 3 with a gloved hand, generally the right hand and fits the operation unit 2 on one finger.

According to the illustrated example, the middle finger engages and is able to operate both the ring 6C of a handle 3 and the operation unit 2. In this way, a user is able to operate an operation group according to the present invention completely by means of one hand, optionally by means of one finger.

Thus, the user brings the pin 9 and the support 10 into the open position A and folds a Y portion of the medical device D in a U-shape (FIG. 10), which protrudes between the handle 3 and the entrance of the endoscope E.

He/she inserts the Y portion folded in a U-shape in the housing 28 of the operation unit 2 (FIG. 11).

He/she pushes the pin 9 and the support 10 into the closed position B (FIG. 12), so as to constrain the medical device D to the operation unit 2, without play, this ensures that the medical device D is as integral as possible (seamless) with the user's finger maximizing control precision of the medical device D.

Advantageously, as shown in FIG. 14, the medical device D is in contact, in use, with the user's (gloved) finger. In this way, the user's sensibility is significantly increased.

Advantageously, if it is necessary to comprise a change of medical device D, the pin 9 and the support 10 are brought into the open position A. The medical device D is removed from the housing 28 leaving the housing 28 free for the insertion of a Y portion of another medical device D.

According to a further variation, not shown, the operation unit 2 is configured to be connected directly, or by intermediate connection means, to the entrance mouth of an endoscope.

An operation group according to the present invention is shown in FIG. 18 comprising a handle 3 and a variant of the operation unit 2. A first variant of the operation unit 2 illustrated in FIG. 18 is shown in detail in FIGS. 19 and 20.

The supporting body 7 is indicated with 121 in FIGS. 19 and 20.

A second variant of the operation unit 2 is shown in detail in FIGS. 21 and 22. The supporting body is indicated with 121' in FIGS. 21 and 22. The operation unit 2 comprises a retaining portion. The retaining portion is fixed to the supporting body.

The retaining portion could be made in a single body with the supporting body. In the examples shown, the retaining portion is made in a single body with the supporting body.

The retaining portion is configured to define a retaining condition of the sheath C. In such retaining condition of the sheath C, such axial movement of the sheath C can be caused by a corresponding movement of said supporting body. Such retaining condition of the sheath C could be a condition of fixing the sheath C to the retaining portion and, consequently, a condition of fixing the sheath C to the supporting body and, consequently, a condition of fixing the sheath C to the operation unit 2.

In this case, the retaining portion could be considered a fixing portion of the sheath C to the operation unit 2 and/or to the supporting body and/or to the retaining portion.

As regards the first variant, the retaining portion is indicated, in particular in FIGS. 19 and 20, with 122a. As regards the second variant, the retaining portion is indicated, in particular in FIGS. 21 and 22, with 122a'. The retaining portion defines a housing, to allow, by means of positioning a sector of said sheath C in said housing, a condition of insertion of said sheath C through said retaining portion. Such housing could pass through from one side to the other of said retaining portion. In the examples shown in figures from 19 to 22, such housing passes through from one side to the other of the retaining portion.

As regards the first variant, such housing is indicated, in particular in FIG. 20, with 1221. As regards the second variant, such housing is indicated, in particular in FIGS. 21 and 22, with 1221'.

The retaining portion comprises retaining means for exerting a retaining action on said sheath C, so that said condition of insertion of the sheath C through the retaining portion corresponds to said retaining condition of the sheath C. Such retaining action could be a fixing action.

As regards the first variant, such retaining means are indicated, in particular in FIGS. 19 and 20, with 1222a. As regards the second variant, such retaining means are indicated, in particular in FIGS. 21 and 22, with 1222a'. Such retaining means could be considered as means of fixing the sheath C to the operation unit 2 and/or to the supporting body 7 and/or to the retaining portion.

The retaining portion is configured, in all of the aforesaid variants, to allow a user to obtain said condition of insertion of the sheath C through the retaining portion, by means of an insertion movement transverse to the elongation of said sheath C.

The first variant provides for that the retaining means 1222a are with interference and configured so that said insertion movement can be caused in contrast to the interference of said retaining means 1222a. In this case, the retaining means 1222a or 1222b are configured so that said retaining action on the sheath C is exerted by means of the conformation of said retaining means 1222a.

In the first variant, the retaining means 1222a could be of the cleat type.

According to the example illustrated in FIGS. 17 and 18, the operation group 1 comprises an operation unit 2 and a handle 3, which differ from each other. Advantageously, in this case, the handle 3 can be any handle.

Advantageously, the sizes of the operation unit 2 are configured to allow the passage through a ring 6 of a handle 3 actuator 5 generally in use.

According to the example illustrated in FIG. 25, an operation unit 2 of the type described above is connected by means of a connector 60 to a handle 3 of the known type (for example a handle with three rings currently already in use), so as to form an operation group 1c. The connector 60 can be made of a single piece or of several pieces and it can be assemblable or made in one piece with the operation unit 2 and/or with the handle 3. Advantageously, in this case, the operation unit 2 is supported, in use, by the handle 3 and it is not necessary for a user to insert a finger inside the operation unit 2.

A further embodiment of a manual operation group according to the present invention is indicated in FIGS. 23 and 24 with 1b. According to the illustration in FIG. 23, the operation unit 12b' comprises an assembly body (indicated in FIG. 23 with 123) configured to be coupled to a handle 3 of the known type.

Preferably, the operation group 1b comprises connection means 125 configured to fix said assembly body 123 to the handle 3. According to the illustrated example, the connection means 125 are releasable means, for example screws or similar. According to one variant, not shown, the assembly body 123 is made in one piece with the handle 3.

According to the operation group 1b, the supporting body of the operation unit is not configured to be applied directly to a hand, in particular fitted to a user's finger. In this case, the supporting body mainly has the function of supporting the retaining portion.

In other words, according to the embodiment shown in FIG. 23, the operation unit is constrained and/or fixed to the handle 3 so that the movement of the handle 3 (arrows z in FIG. 23) can cause, in turn, a corresponding movement of the operation unit 2 (arrows w in FIG. 23).

The assembly system 125 comprises a hole, which extends along a longitudinal axis and is defined by said assembly body 123. According to the example shown in FIG. 23, the assembly system 125 comprises a tightening element 1252 for tightening said assembly body 123 about said portion of the handle 3, while said handle 3 assumes said condition of insertion of the handle 3 through said assembly body 123 so as to complete the attainment of the aforesaid assembly condition.

When said supporting body 121b' and said assembly body 123 assume said condition of connection and said assembly body 123 assumes said condition of assembly on the handle 3 said retaining portion 122b' is spaced apart with respect to said handle 3 along a direction, which is transverse and/or orthogonal to said longitudinal axis.

In this way, the retaining portion 122b' can retain a sector of the sheath C, which is sufficiently close to the entrance of the sheath C in the endoscope E, so that the aforesaid movement of the supporting body 121b' causes the axial movement of the sheath C efficiently along the tube T of the endoscope E. In fact, a long section of the sheath C could be present, as shown in FIG. 1, between the handle 3 and the entrance of the sheath C in the endoscope E. Given that such section could be at least partially loose, the length of such section could in fact make the correlation between the movement of the supporting body 121b' and the axial movement of the sheath C difficult along such tube T. Whereas, such positioning of the retaining portion 122 b' spaced apart along a transverse direction allows the retaining portion 122b' to retain the sheath C sufficiently close to the entrance of the sheath C in the endoscope E.

An operation unit 2 of an operation group 1 according to the present description allows the flexibility of the sheath C to be used effectively and to this purpose.

In fact, by arranging the sheath C in a curved manner, in a section of the same upstream of the endoscope E, and roughly, for example in a circle, it is possible to exploit such curved positioning, to cause the retaining portion to retain the sheath C sufficiently close to the entrance thereof in the endoscope E, to obtain the aforesaid effect in terms of efficacy in order to obtain the axial movement of the sheath C, and consequently of the operating instrument S along the tube T, by moving the supporting body 7.

Such situation can be obtained both with the first embodiment of the operation group 1, as shown in FIGS. 17 and 18, and with the second embodiment of the operation group 1*b*, as may be concluded from FIG. 23.

The assembly body 123 could be made in a single body with said supporting body 121*b*', so that said supporting body 121*b*' and said assembly body 123 permanently assume said condition of connection. In this case, such connection means 124 comprise a transition area located between said assembly body 123 and said supporting body 121*b*'. The connection means 124, as shown in FIG. 11, could be configured to allow a user to cause a rotation of said supporting body 121*b*' with respect to said assembly body 123. In this way, while said supporting body 121*b*' and said assembly body 123 assume said condition of connection and said assembly body 123 assumes said condition of assembly on the handle 3, such user can vary the orientation of said supporting body 7, 121*b*' with respect to said handle 3, in order to adapt said orientation to the specific needs. Alternatively, the aforesaid transition area between the assembly body 123 and the supporting body 121*b*' could be a weakened structural portion to allow a user to cause said rotation.

According to the illustrated examples, the supporting body 7, 121 or 121' is a thimble, which can be fitted and/or fixed to the (gloved) finger of said user, so that such user can cause said movement of the supporting body 7, 121 or 121' with such finger, and thus also such axial movement of the sheath C. Consequently, in the first variant shown in FIGS. 19 and 20, the supporting body 121 defines a through cavity in the supporting body 121, to allow such thimble to be fitted stably to a user's finger. An example of a finger to which the thimble could be configured to be fitted is indicated with F in FIG. 17 and in FIG. 18. As can be seen in FIG. 18, such thimble could be configured to be fitted stably to a ring finger. As shown in FIG. 17, the operation unit 2 can be fitted to the middle finger, which can also be used simultaneously to operate the handle 3.

As regards the first variant, such cavity 21 is indicated, in detail, in FIGS. 19 and 20, with 1211.

As regards the second variant, such cavity is indicated, in detail, in FIGS. 21 and 22, with 1211'.

The fact that the supporting body 7, 121 or 121' is a thimble allows the retaining portion 122*a* or 122*a*' to retain a sector of the sheath C sufficiently close to the entrance of the sheath C in the endoscope E, so as to allow the aforesaid movement of the supporting body 7, 121 or 121' to cause an axial movement of the sheath C effectively along the tube T of the endoscope E.

The difference between the first embodiment of the operation group 1 (FIGS. 17 and 18) and the second embodiment of the operation group 1*b* (FIG. 23) is that:

in the operation group 1, the supporting body 7, 121 or 121' is a thimble (a closed or at least partially open annular body), which is independent of the handle and allows a user to cause such movement of the supporting body 7 121 or 121', and thus also the axial movement of the sheath C along the tube T of the endoscope E, and thus also the axial movement of the operating instrument S along such tube T, by means of the finger F to which the thimble is fitted and belonging to the same hand M, which operates the operating instrument S by acting on the handle 3;

in the operation group 1*b*, when the supporting body 121*b*' assumes the condition of connection to the assembly body 123 and the same assembly body 123 assumes the condition of assembly on the handle 3, the operation unit 12*b*' is integral with the handle 3, so that a user can cause said movement of the supporting body 121*b*' (and thus also the axial movement of the sheath C along the tube T of the endoscope E, and thus also the axial movement of the operating instrument S along such tube T) by acting on the handle 3 or directly on the supporting body 121*b*'.

The first embodiment of the operation group 1 (FIGS. 17 and 18) allows a user to operate the operating instrument S, while other fingers of such hand M are engaged with the at least one actuator 5 of the handle 3, also causing the axial movement of the sheath C by means of the supporting body 7, 121 or 121', along the tube T of the endoscope E, and thus also the axial movement of the operating instrument S along the tube of the endoscope E, so as to be able to regulate the positioning of the distal end s2 of the operating instrument S in the patient body, if necessary, also simultaneously with the actuation of the operating instrument S, and in any case with the same hand (advantageously with one finger, which is also engaged in operating the handle 3), causing such actuation of the operating instrument S.

The second embodiment of the operation group 1*b* (FIG. 23) allows the operation unit 12*b*' to be supported, in the condition of assembly of the assembly body 123 on the handle 3 and in the condition of connection 124 between the supporting body 121*b*' and the assembly body 123, by the same handle 3, which is supported, in turn, by the fingers, which are engaged with the at least one actuator 5. Consequently, in this case, the user can cause the axial movement of the sheath C along the tube T, and thus the axial movement of the operating instrument S along the tube T, with the same fingers, which are engaged with the at least one actuator 5, operating the operating instrument S also simply by pushing the operation unit 12*b*' without having to fit the operation unit 12*b*' to one finger.

Consider that, in general, according to the first embodiment of the operation group 1 (FIGS. 17 and 18) the supporting body 7, 121 or 121' could be configured to be fitted stably and/or fixed to any part of such hand M, so as to obtain the aforesaid effects in terms of possibility of moving the sheath C axially along the tube T of the endoscope E with the same hand M, which operates the operating instrument S.

Consequently, the first embodiment 1 of the operation group and the second embodiment 1*b* of the operation group differ from each other in the configuration of those technical aspects of the operation unit 2, 12*b*', which allow the advantageous possibility to be obtained of causing the axial movement of the sheath C with the same hand M, which operates the device D.

It is further specified that for the first embodiment of the operation group 1, the variations of the operation unit 2 differ from one another substantially in the configuration of the retaining portion, the adjustment unit and in the retaining means, and consequently in those technical aspects of the operation unit 2, which allow the definition of the causal correlation between the movement of the supporting body 7 and the axial movement of the sheath C, which movement of the supporting body 7 can be caused, in turn, according to the above, by means of the same hand, advantageously one same finger, which operates the handle 3.

An operation group 1 according to the present description thus comprises an operation unit 2 of the sheath, which can be brought by the same hand, which supports said handle 3, to allow the user to operate, at will, simultaneously or not, the at least one actuator 5 of the handle 3 and the operation unit 2, with the consequent actuation of the operating instrument and axial movement of the sheath C, and thus also of the operating instrument, along the tube of the endoscope E, so as to obtain, in a more efficient manner, with the same hand M, both the operating movement of the operating end s2 and the change in position of the operating end s2 with respect to a volume inside the patient body, in which the operating end s2 is designed to operate.

In a certain sense, the operation unit 2 could be considered part of the handle 3.

A medical operating kit according to the present description comprises at least one endoscope E and an operation group 1, 1*b*, 1*c* according to the present description. Such medical kit could also comprise at least one further component, as shown in FIG. 17 or in FIG. 18.

It could be that before entering the endoscope E and exiting the same, with the aforesaid distal end sector, the device D also passes through such at least one further component.

An example of the importance of the present invention is given by the case, wherein the operating instrument is represented by a diathermic polypectomy snare of the colon.

The procedure is characterised by the capture and subsequent cutting of the wound.

In this case the sheath C is a catheter.

Capture consists of comprising the polyp inside the snare, the opening and closing of which is determined by the outward sliding of the catheter of the same, which is determined by the actuators of the handle 3. To capture the polyp, after correctly positioning the endoscope E, the opening and closing of the snare is required, which is implemented by the handle 3, associated with movements, in a proximal and distal direction, with respect to the end of the endoscope E, of the catheter. Such manoeuvres must comprise a significant coordination. Similarly, in the cutting step, which is obtained, after capturing the polyp by gradually closing the snare, according to the response of the tissue, opportune variations in the pressure exerted on the handle 3 are required. During closure of the snare it is also opportune to make coming and going movements with the snare, both to favour the detachment of the wound from the cleavage plane thereof and to reduce the thermal damage to the deeper layers of the intestinal wall.

According to the technology of the prior art, since the endoscopist uses one hand to manoeuvre the endoscope E, normally, with the second hand, he/she can operate only one of the two operating actions needed to implement the procedure, i.e. the movement of the catheter to which the operating instrument is constrained, introduced into the body by means of the endoscope E, and the actuation of the actuators on the handle 3. Thus, the latter action is generally carried out by an assistant, mostly not a doctor, usually a nurse. Clearly, it is understandable how important it is to have complete harmony between the two users and how essential it is that orders given by the doctor are not only clear and comprehensible, but also translated exactly by the assistant.

The operation group 1, 1*b*, 1*c* overcomes these problems. Advantageously, by means of an operation group 1, 1*b*, 1*c* according to the present description, the doctor can perform all of the operations needed to move the medical device D along the tube T of the endoscope E, and actuate the medical device D, also simultaneously, alone, and with the same hand.

Advantageously, the operation unit 2, 12*b*' of the type described above, can be used in conjunction with any handle 3. Consequently, the operation unit 2, 12*b*' can be supplied separately to implement operating kits already in use.

Advantageously, the operation unit 2, 12*b*' of the type described above, allows the medical device D to be operated directly, i.e. without the interposition of further elements, for example without the interposition of: motors, servo controls, levers or similar. In this way, the operation unit 2, 12*b*' guarantees the user maximum sensibility and maximum operating precision of the medical device D, in particular when generating the axial movement of the sheath G of a medical device D, which can be used on an endoscope E and along a tube T of an endoscope E, in response to axial movements given to the sheath C along the tube T.

Advantageously, the operation unit 2, 12*b*' of the type described above, ensures the user can perform all of the necessary operations during an endoscopy with only one hand M, at the same time guaranteeing maximum freedom of movement/articulation of the user's hand M.

Advantageously, the operation unit 2, 12*b*' of the type described above, allows a user to perform several different operations with one single finger F, which nonetheless has maximum freedom of articulation.

Advantageously, the operation unit 2, 12*b*' of the type described above, can be applied to handles 3 of the type already commonly in use, which are pre-integrated or assemblable with a medical device D, without making any changes to the structure of the handle 3 itself or to the functionality thereof.

The operation unit 2, 12*b*' of the type described above, allows maximum freedom of movement of the user's hand, without limiting the bending and stretching movements thereof. Advantageously, the operation unit 2, 12*b*' of the type described above, doesn't involve other fingers for the movement thereof, in other words, it leaves maximum freedom of movement for all of the fingers of the hand. Therefore, due to the operation unit 2, 12*b*' of the type described above, it is easy for a user to grip and operate any type of handle/medical device assembled to any type of handle, thus constituting an operation group 1, 1*b*, 1*c* of the type described above, wherein the user's hand acts as a means of communication between the operation unit 2, 12*b*' and the handle 3.

Advantageously, therefore, the operation unit 2, 12*b*' of the type described above, allows the use of handles currently already in use, thus maintaining the general executive procedures commonly described in literature, since the structure of the medical device D and the handle 3 are unaltered with respect to those already in use. In this sense, the operation unit 2, 12*b*' allows all of the operations to be transferred to the management of one single hand. Consequently, the operation unit 2, 12*b*' of the type described above, allows the already existing protocols of use to be maintained for the medical devices D and the handles 3 in commerce (from the techniques described with the existing accessories/medical devices to the cutting and coagulation current method), making a significant improvement to the same in terms of sensibility and safety.

Therefore, by means of the operation unit 2, 12*b*' of the type described above, the operating protocols and implementing methods for the operating movements remain unchanged, minimising the risks.

Advantageously, it is evidenced how the operation unit makes the finger, in particular the ungual phalanx substantially integral with the sheath C. Furthermore, it is evidenced how the finger, in particular the ungual phalanx, is particularly receptive and, thus, due to the operation unit 2, the user is able to perceive direct sensations of the exact resistance of the tissues on the medical device D.

Advantageously, the operation unit 2 of the type described above, can be adapted both to any user (size of a user's fingers) and to any type of handle currently on the market.

Advantageously, the operation unit 2 is of the disposable type with a contained economic cost. This guarantees the use of an operation unit 2 exclusively for an operation with consequent advantages of safety and preventing infections.

Advantageously, the operation unit 2 has a highly reduced volume, with consequent advantages of storage and transport.

The invention claimed is:

1. A manual operation unit (2) configured to operate without the aid or the interposition of motors or servo controls, directly, with only one hand, or with a single finger, the axial movements of a medical device (D), which can be used on an endoscope (E); wherein, the medical device (D) comprises an elongated sheath (C) having a proximal end (c1) and a distal end (c2), and an operating instrument(S) inserted through and constrained, at least partially, to said sheath (C), so that an axial movement of said sheath (C) along a tube (T) of said endoscope (E) causes a corresponding axial movement of said operating instrument(S) along said tube (T), said axial movement of the operating instrument(S) thus being able to correspond to the variation of a positioning of an operating end (s2) of said instrument(S) with respect to a volume inside the patient's body; wherein said operating instrument(S) is capable of further activation movements independent of the axial movement of said sheath (C); wherein said operation unit (2) comprises:
a supporting body (7; 121; 121'; 121b'), which is configured to come into contact, in use, with an area, or a finger, of a user's gloved hand; and
a retaining portion (8; 122a; 122a'; 122b'), which is connected on said supporting body (7; 121; 121'; 121b') and configured to slidably receive said sheath (C) of the medical device (D) therethrough, at a position along the sheath (C), so that the sheath (C) extends through the retaining portion, so as to generate a corresponding axial movement of the sheath (C) within said endoscope (E), by moving the supporting body (7) relative to said endoscope (E).

2. The manual operation unit according to claim 1, wherein the supporting body (7; 121; 121') is configured to be fitted, in use, about a finger of a user's hand, so that a movement of said finger can generate a consequent movement of said supporting body (7; 121; 121'); wherein the supporting body (7; 121; 121') comprises a curved wall (20) having a longitudinal axis (X), an inner surface (21), an outer surface (22), a proximal surface (23), and a distal surface (24).

3. The manual operation unit according to claim 2, wherein said curved wall (20) has a housing (28), which is configured to house, in use, a portion (Y) of said medical device (D); wherein said housing (28) is a through housing that cuts said curved wall (20) radially; wherein said housing (28) faces outwardly through an inner opening (31) and an outer opening (32) made on the inner surface (21) and on the outer surface (22) of the curved wall (20) respectively; wherein said housing (28) is sized to allow the medical device (D) to face or protrude, in use, onto/from said inner opening (31), so as to favor the contact between the medical device (D) and the user's finger.

4. The manual operation unit according to claim 3, wherein said housing (28) is substantially transverse to said longitudinal axis (X) and arranged at a center position with respect to the longitudinal axis (X) of the curved wall (20); wherein said housing (28) divides the curved wall (20) in a proximal part (29) and a distal part (30); the extension along said longitudinal axis (X) of the distal part (30) is from 2 to 4 cm.

5. The manual operation unit according to claim 3, wherein the retaining portion (8) is connected by said supporting body (7), so as to be mutually movable from an open configuration, wherein it is possible to insert or remove a portion (Y) of said medical device (D) in the housing (28), to a closed configuration, wherein a medical device (D) is locked in the housing (28) or cannot be inserted into said housing (28).

6. The manual operation unit according to claim 3, wherein the supporting body (7) has a through cavity (33), which extends along said longitudinal axis (X) from the proximal surface (23) to the distal surface (24), facing outside said supporting body (7) through a proximal opening (34) and a distal opening (35) respectively; wherein said operation unit (2) comprises a pin (9), which is mounted slidably in said cavity (33) from an open position (A) to a closed position (B), and vice versa; wherein said pin (9) is configured to cross said housing (28) transversely.

7. The manual operation unit according to claim 6 and comprising a support (10), which is fixed to said pin (9); wherein said support (10) is movable with said pin (9) from the open position (A) to the closed position (B), and vice versa; wherein said support (10) is configured to extend along the outer surface (22) parallel to the longitudinal axis (X), so as to lock the medical device (D) in said housing (28) when the support (10) is in the closed position (B).

8. The manual operation unit according to claim 1, wherein the retaining portion (8) is movably mounted with respect to the supporting body (7).

9. The manual operation unit according to claim 1, wherein the supporting body (7) is open and delimited at the side by a right side surface (25) and a left side surface (26), which define a first end (I) and a second end (II), spaced apart from each other, of said supporting body (7); wherein said operation unit (2) comprises an adjustment unit (27), which connects said first end (I) to said second end (II) and is configured to adapt the operation unit (2) to the sizes of the fingers to which it is applied, so as to maximize a surface of the operation unit (2) and/or of the medical device (D) in contact with the user's finger.

10. The manual operation unit according to claim 1, further comprising:
a handle (3)
an assembly body (123);
an assembly system (125) for defining a condition of assembly of said assembly body (123) on said handle (3) actuated by a hand (M);
a connector (124) for defining a condition of connection between said assembly body (123) and said supporting body (7; 121b; 121b'), so that, in said condition of connection between said assembly body (123) and said supporting body (121b'), said movement of the supporting body (121b') can be caused by the user's finger and/or a corresponding movement of said handle (3).

11. The manual operation unit according to claim 10, wherein said assembly system (125) comprises:
a hole, which extends along a longitudinal axis (X), defined by said assembly body (123), so as to allow, by positioning a portion of said handle (3) in said hole, a condition of insertion of the handle (3) through said assembly body (123);

a tightening element (1252) for tightening, in said condition of insertion of the handle (3) through the assembly body (123), said assembly body (123) about said portion of the handle (3);

said operation unit (12b') being configured so that, in said condition of assembly of the assembly body (123) on the handle (3) and in said condition of connection between said supporting body (7; 121b; 121b') and said assembly body (123), said retaining portion (122b') is spaced apart with respect to the handle (3) along a direction, which is transverse and/or orthogonal to said longitudinal axis (X).

12. The manual operation unit according to claim 10, wherein said connector (124) is configured to allow a user to cause a rotation of said supporting body (121b') with respect to said assembly body (123), so as to vary, in said connection of assembly of the assembly body (123) on the handle (3) and in said condition of connection between the supporting body (121b') and the assembly body (123), the orientation of said supporting body (121b') with respect to said handle (3), to adapt said orientation to any specific need.

13. The manual unit according to claim 10, wherein said assembly body (123) is made in a single body with said supporting body (121b'), so that said supporting body (7; 121b') and said assembly body (123) permanently assume said condition of connection, said connector (124) comprising a transition area located between said assembly body (123) and said supporting body (121b').

14. The manual operation unit according to claim 13, wherein said transition area is a weakened structural portion, to allow a user to cause said rotation.

15. The manual operation unit according to claim 1, wherein said retaining portion (122a; 122a'; 122b') comprises:
a housing (1221; 1221'; 1221b') having a retainer for positioning a sector of said sheath (C) in said housing (1221; 1221'; 1221b') through an insertion motion;
the retainer (1222a; 1222a'; 1222b') being configured for exerting a retaining action on said sheath (C).

16. The manual operation unit according to claim 15, wherein said retaining portion (122a; 122a'; 122b') is configured to allow a user to obtain said retaining action of the sheath (C) by the insertion motion of said sector of the sheath into said retainer of said housing (1221; 1221'; 1221b').

17. The manual operation unit according to claim 16, wherein said retaining portion (122a; 122a'; 122b') is configured so that said insertion motion is transverse to the elongation of said sheath (C).

18. The manual operation unit according to claim 16, wherein said retainer (1222a; 1222a'; 1222b') is configured to produce said retaining action with interference and is configured so that:
said insertion motion can be caused in contrast to the interference of said retainer;
said retaining action is exerted by the conformation of said retainer (1222a; 1222a'; 1222b').

19. The manual operation unit according to claim 18, wherein said retainer (1222a; 1222a'; 1222b') is of the cleat type.

20. The manual operation unit according to claim 1, configured to engage only one phalanx of a user's finger of any size.

21. A manual operation group comprising a handle (3) and the manual operation unit (2; 12b') according to claim 1.

22. The manual operation group according to claim 21, wherein said handle (3) and said operation unit (2; 12b') are connected to each other.

23. The manual operation group according to claim 22, wherein said handle (3) and said operation unit (2; 12b') are connected to each other by a connector (60; 123).

24. The manual operation group according to claim 21, wherein:
said handle (3) is configured to allow a user to cause the actuation of said operating instrument(S); acting on at least one actuator (5) of said handle (3) with one hand (M), while said device (D) assumes such condition of attachment, said actuation of the device (D) corresponding to an operating movement of said operating end (s2);
said operation unit (2; 12b') is configured to allow the user to cause, with the same hand (M), or with a finger, or, simultaneously with said actuation, also said axial movement of the sheath (C), so as to be able to cause, with said hand (M) or also simultaneously, both the actuation of the device (D) and said variation of positioning of said operating end (s2);
wherein the operation unit (2; 12b') is configured to allow the user to act directly, without interposition of motors, servo controls or levers, on said sheath (C) and, consequently, on tissues, which are intended to be treated, so that a consistency and resistance of the tissues are immediately perceived by the user.

25. A manual operation unit (2) configured to operate without the aid or the interposition of motors or servo controls, directly, with only one hand, or with a single finger, the axial movements of a medical device (D), which can be used on an endoscope (E); wherein, the medical device (D) comprises an elongated sheath (C) having a proximal end (c1) and a distal end (c2), and an operating instrument(S) inserted through and constrained, at least partially, to said sheath (C), so that an axial movement of said sheath (C) along a tube (T) of said endoscope (E) causes a corresponding axial movement of said operating instrument(S) along said tube (T), said axial movement of the operating instrument(S) thus being able to correspond to the variation of a positioning of an operating end (s2) of said instrument(S) with respect to a volume inside the patient's body; wherein said operating instrument(S) is capable of further activation movements independent of the axial movement of said sheath (C); wherein said operation unit (2) comprises:
a supporting body (7; 121; 121'; 121b'), which is configured to come into contact, in use, with an area, or a finger, of a user's gloved hand; and
a retaining portion (8; 122a; 122a'; 122b'), which is connected to said supporting body (7; 121; 121'; 121b') and configured to hook, in use, to said sheath (C) of the medical device (D), at a position along the sheath (C), so as to generate a corresponding movement of the sheath (C) relatively to said endoscope (E), by moving the supporting body (7) relatively to said endoscope (E);
wherein the supporting body (7; 121; 121') is configured to be fitted, in use, about a finger of a user's hand, so that a movement of said finger can generate a consequent movement of said supporting body (7; 121; 121');
wherein the supporting body (7; 121; 121') comprises a curved wall (20) having a longitudinal axis (X), an inner surface (21), an outer surface (22), a proximal surface (23), a distal surface (24); and
wherein said curved wall (20) has a housing (28), which is configured to house, in use, a portion (Y) of said medical device (D); wherein said housing (28) is a through housing that cuts said curved wall (20) radially; wherein said housing (28) faces outwardly through an inner opening (31) and an outer opening (32) made on the inner surface (21) and on the outer surface (22) of the curved wall (20) respectively; wherein said housing (28) is sized to allow the medical device (D) to face or protrude, in use, onto/from said inner opening (31), so as to favor the contact between the medical device (D) and the user's finger.

26. A manual operation unit (2) configured to operate without the aid or the interposition of motors or servo controls, directly, with only one hand, or with a single finger, the axial movements of a medical device (D), which can be used on an endoscope (E); wherein, the medical device (D) comprises an elongated sheath (C) having a proximal end (c1) and a distal end (c2), and an operating instrument(S) inserted through and constrained, at least partially, to said sheath (C), so that an axial movement of said sheath (C) along a tube (T) of said endoscope (E) causes a corresponding axial movement of said operating instrument(S) along said tube (T), said axial movement of the operating instrument(S) thus being able to correspond to the variation of a positioning of an operating end (s2) of said instrument(S) with respect to a volume inside the patient's body; wherein said operating instrument(S) is capable of further activation movements independent of the axial movement of said sheath (C); wherein said operation unit (2) comprises:

a supporting body (7; 121; 121'; 121b'), which is configured to come into contact, in use, with an area, or a finger, of a user's gloved hand; and a retaining portion (8; 122a; 122a'; 122b'), which is connected to said supporting body (7; 121; 121'; 121b') and configured to hook, in use, to said sheath (C) of the medical device (D), at a position along the sheath (C), so as to generate a corresponding movement of the sheath (C) relatively to said endoscope (E), by moving the supporting body (7) relatively to said endoscope (E);

wherein said retaining portion (122a; 122a'; 122b') comprises a housing (1221; 1221'; 1221b') having a retainer for positioning a sector of said sheath (C) in said housing (1221; 1221'; 1221b') through an insertion motion, the retainer (1222a; 1222a'; 1222b') being configured for exerting a retaining action on said sheath (C); and wherein said retaining portion (122a; 122a'; 122b') is configured to allow a user to obtain said retaining action of the sheath (C) by the insertion of said sector of the sheath into said housing (1221; 1221'; 1221b'), and said retaining portion (122a; 122a'; 122b') is configured so that said insertion motion is transverse to the elongation of said sheath (C).

\* \* \* \* \*